United States Patent
Pan et al.

(10) Patent No.: US 8,951,403 B2
(45) Date of Patent: Feb. 10, 2015

(54) DETECTION METHOD FOR SENSOR MEMBRANE OF EUROPIUM TITANIUM OXIDE AS PART OF A BIOSENSOR BY USING PNIPAAM FOR WRAPPING ENZYMES

(75) Inventors: Tung-Ming Pan, Taipei (TW); Chao-Wen Lin, Puli Township, Nantou County (TW); Kung-Yuan Chang, Caotun Township, Nantou County (TW); Min-Hsien Wu, Kaohsiung (TW); Shiao-Wen Tsai, Taipei (TW)

(73) Assignee: Chang Gung University, Taoyuan (TW)

( * ) Notice: Subject to any disclaimer, the term of this patent is extended or adjusted under 35 U.S.C. 154(b) by 218 days.

(21) Appl. No.: 13/478,161

(22) Filed: May 23, 2012

(65) Prior Publication Data

US 2013/0032492 A1 Feb. 7, 2013

(30) Foreign Application Priority Data

Aug. 5, 2011 (TW) .............................. 100127898 A

(51) Int. Cl.
*G01N 27/327* (2006.01)
*C12Q 1/00* (2006.01)
*G01N 27/22* (2006.01)

(52) U.S. Cl.
CPC .............. *C12Q 1/001* (2013.01); *G01N 27/227* (2013.01)

USPC ...................................... 205/778; 204/403.05

(58) Field of Classification Search
CPC ........................................... C12Q 1/002–1/003
USPC ......... 204/400, 403.04, 403.05; 205/775, 778
See application file for complete search history.

(56) References Cited

PUBLICATIONS

Pan et al., Sensors and Actuators B 160, 2011, 850-857.*
Zhang et al., J.Mater. Chem., 2003, 13, 2261-2265.*
Sagoff, J; New classes of magentoelectric materials promise advances in computing technology, Argonne National Laboratory; Feb. 2013.*

* cited by examiner

*Primary Examiner* — Luan Van
*Assistant Examiner* — Gurpreet Kaur

(57) ABSTRACT

A detection method for a sensor membrane formed of europium titanium oxide as part of a biosensor by using PNIPAAm for wrapping enzymes includes adding 1.0 g of NIPAAm powder to 20 ml water, heating same at 60° C. to form NIPAAm solution, and cooling the NIPAAm solution; adding 200 μl of 98.7 wt % of APS and 50 μl of 99 wt % of TEMED to the NIPAAm solution, uniformly mixing same, and reacting the mixture for 30 hours to prepare a transparent, gel PNIPAAm; adding 5 mg enzymes to 100 μl of 1×PBS buffer solution, uniformly mixing same, adding 100 μl of PNIPAAm to the buffer solution, and uniformly mixing the buffer solution; placing a biosensor on a heater for heating at a constant temperature of 37° C. with the biosensor being an EIS sensor having a sensor membrane formed of $EuTi_xO_y$; and taking a measurement.

2 Claims, 5 Drawing Sheets

DETECTION METHOD FOR SENSOR MEMBRANE OF EUROPIUM TITANIUM OXIDE AS PART OF A BIOSENSOR BY USING PNIPAAM FOR WRAPPING ENZYMES

BACKGROUND OF THE INVENTION

1. Field of the Invention

The invention relates to biosensors and, more particularly, to a detection method for sensor membrane of europium titanium oxide as part of a biosensor by using PNIPAAm for wrapping enzymes to increase sensitivity and improve reliability of the biosensor.

2. Description of Related Art

Acid alkaline sensors and biosensors are widely employed for chemical analysis and physical examination in recent years. They cooperate with an enzyme membrane and other enzyme fixing methods for examining changes of the physical body including urine tests, blood glucose tests, etc. Thus, applications are greatly increased.

Ionic field effect transistors are widely used as components of a sensor due to miniature size, quick response time and low cost. Sensors made of ionic field effect transistors are widely used to detect enzymes such as glucose, urea, lactic acid, or uric acid. Enzyme membranes on ionic field effect transistors react with targets to change an acid alkaline value, so that a sensor may sense the changes. Thus, how to secure the enzyme membrane onto the ionic field effect transistors is an issue to be addressed.

Conventionally, enzyme fixing can be done by chemical methods, physical methods, or combinations of chemical and physical methods. However, these conventional methods are disadvantageous due to the following drawbacks. Activities of enzymes are difficult being controlled by chemical methods. Further, enzymes are short lived proteins. Physical methods are done in room temperature and are capable of minimizing the activity loss of enzymes. However, its adhesion is weak, and thus, chemical substances of targets may be lost. Alternatively, seaweed glue is employed to wrap enzymes. However, seaweed glue is not easy to wash after use.

Thus, the need for improvement still exists.

SUMMARY OF THE INVENTION

It is therefore one object of the invention to provide a detection method for a sensor membrane formed of europium titanium oxide as part of a biosensor by using poly-N-isopropylacrylamide (PNIPAAm) for wrapping enzymes, comprising the steps of: (1) adding 1.0 g of N-isopropylacrylamide (NIPAAm) powder to 20 ml water, heating same at 60° C. to form NIPAAm solution, and cooling the NIPAAm solution in room temperature; (2) adding 200 μl of 98.7 wt % of (ammonium peroxodisulfate (APS)) and 50 μl of 99 wt % of N,N,N, N-tetramethylethylenediamine (TEMED) to the NIPAAm solution, uniformly mixing same, and reacting the mixture for 30 hours in room temperature to prepare a transparent, gel PNIPAAm; (3) adding 5 mg enzymes to 100 μl of 1×PBS buffer solution, uniformly mixing same, adding 100 μl of PNIPAAm to the buffer solution, and uniformly mixing the buffer solution; (4) placing a biosensor on a heater for heating at a constant temperature of 37° C. with the biosensor being an Electrolyte-Insulator-Semiconductor (EIS) sensor having a sensor membrane formed of europium titanium oxide; (5) dropping 25 μl PNIPAAm obtained in step (3) on the sensor membrane of the biosensor; (6) heating and curing the biosensor to form a white gel on the sensor membrane; (7) placing the biosensor in a solution kept at 37° C. and keeping the white gel obtained at step (6) at 37° C.; and (8) taking a measurement.

The above and other objects, features and advantages of the invention will become apparent from the following detailed description taken with the accompanying drawings.

DETAILED DESCRIPTION OF THE INVENTION

Figure 1:
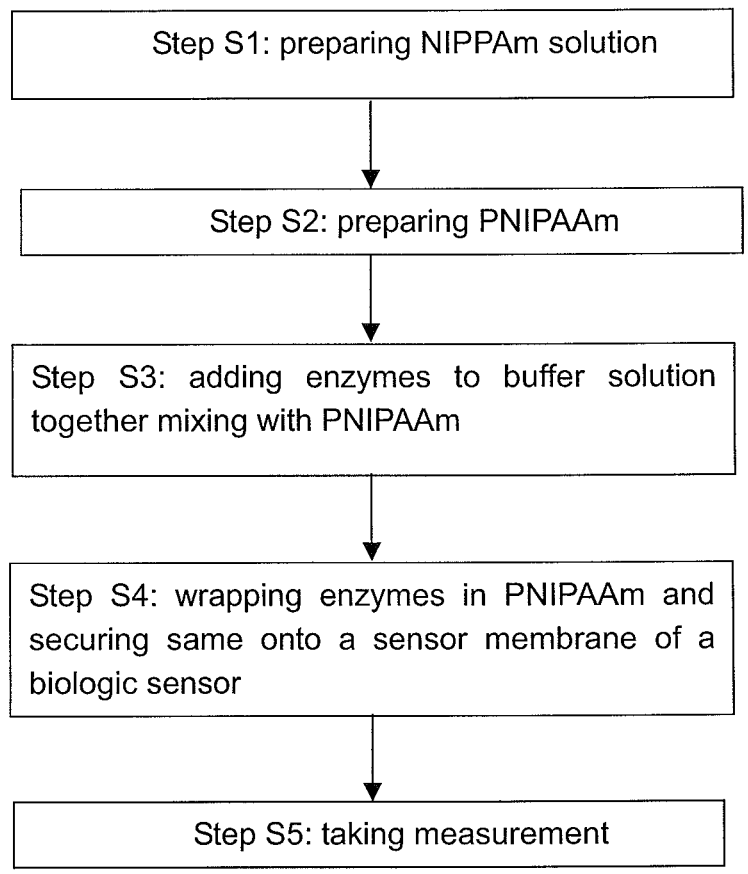
FIG. 1 is a flow chart of a method according to the invention.
Figure 2:
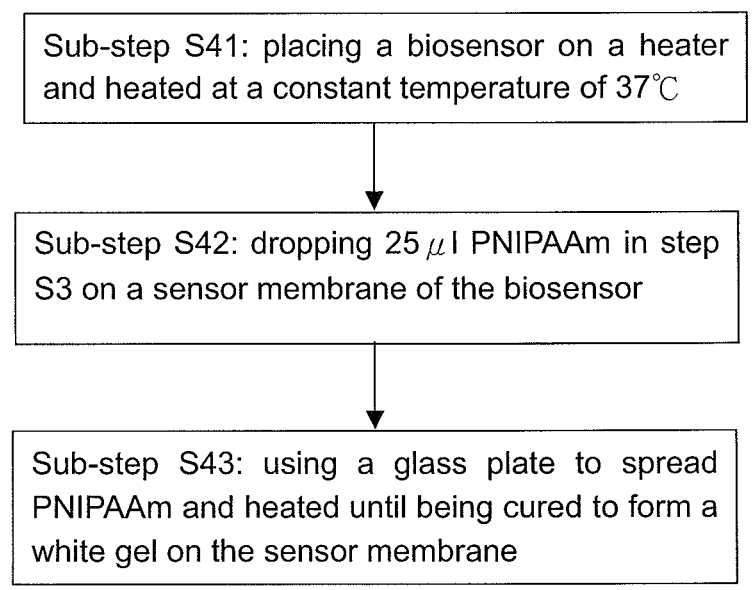
FIG. 2 is a flow chart of sub-steps of the step S4 for illustrating how to wrap enzymes in PNIPAAm to form an enzyme membrane on a sensor membrane.

Referring to FIGS. 1 and 2, a flow chart of a detection method for a sensor membrane of europium titanium oxide as part of a biosensor by using PNIPAAm for wrapping enzymes in accordance with the invention is illustrated. The method comprises the steps of:

Step S1 is preparation of N-isopropylacrylamide (NIPAAm) solution. Add 1.0 g of NIPAAm powder to 20 ml water and heat same at 60° C. to form NIPAAm solution which is in turn cooled in room temperature.

Step S2 is preparation of poly-N-isopropylacrylamide (PNIPAAm). Add 200 μl of 98.7 wt % of ammonium peroxodisulfate (APS) and 50 μl of 99 wt % of N,N,N,N-tetramethylethylenediamine (TEMED) to NIPAAm solution and uniformly mix same. The mixture then reacts for 30 hours in room temperature. As a result, a transparent, gel poly-N-isopropylacrylamide (PNIPAAm) is prepared.

Step S3 is adding enzymes to a buffer solution together mixing with PNIPAAm. Add 5 mg enzymes to 100 μl of 1×PBS buffer solution and uniformly mix same. Next, add 100 μl of PNIPAAm to the buffer solution and uniformly mix same. The enzyme is glucose, urea, lactic acid, or uric acid.

Step S4 is wrapping enzymes in PNIPAAm and securing same onto a sensor membrane of a biosensor. The biosensor is an Electrolyte-Insulator-Semiconductor (EIS) sensor having a sensor membrane of europium titanium oxide. Details of the biosensor are discussed later.

As illustrated in FIG. 2 in conjunction with FIG. 1, step S4 comprises the sub-steps of:

Sub-step S41 is placing a biosensor on a heater for heating at a constant temperature of 37° C.

Sub-step S42 is dropping 25 μl PNIPAAm obtained in step S3 on a sensor membrane of the biosensor.

Sub-step S43 is using a glass plate to spread PNIPAAm and heating same until cured to form a white gel on the sensor membrane.

Turning to FIG. 1 again, in step S5 a measurement is taken. In detail, place the biosensor in a solution kept at 37° C. so that the white gel obtained at sub-step S43 can be kept at 37° C. Next, measurement is taken. Next, the white gel PNIPAAm is cooled to form a liquid PNIPAAm. Finally, wash the liquid PNIPAAm with distilled water.

The one-use PNIPAAm produced by the invention can be employed for wrapping enzymes. Further, an enzyme membrane is formed on the wrapped enzymes due to the nature of PNIPAAm becoming a gel by heating. Next, a measurement can be taken. The gel obtained by the invention can return to a liquid state by cooling. Next, the liquid PNIAAm can be washed away by using distilled water. PNIAAm has high sensitivity and good reliability. PNIAAm can be easily mass prepared by using inexpensive chemicals. Finally, it can be easily washed away after use. All of above advantages and characteristics are not found in the prior art of wrapping enzymes by using seaweed glue.

Figure 3:
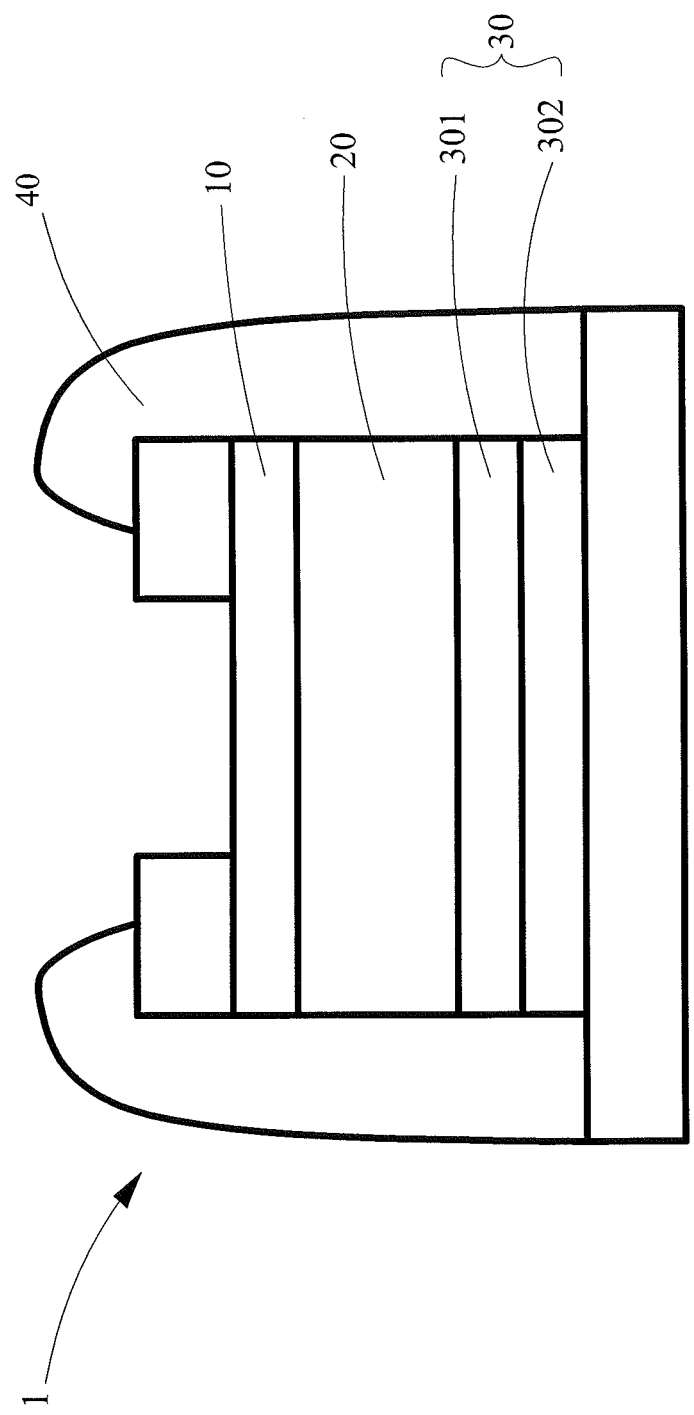
FIG. 3 is a longitudinal sectional view of a biosensor according to the invention.
Figure 4:
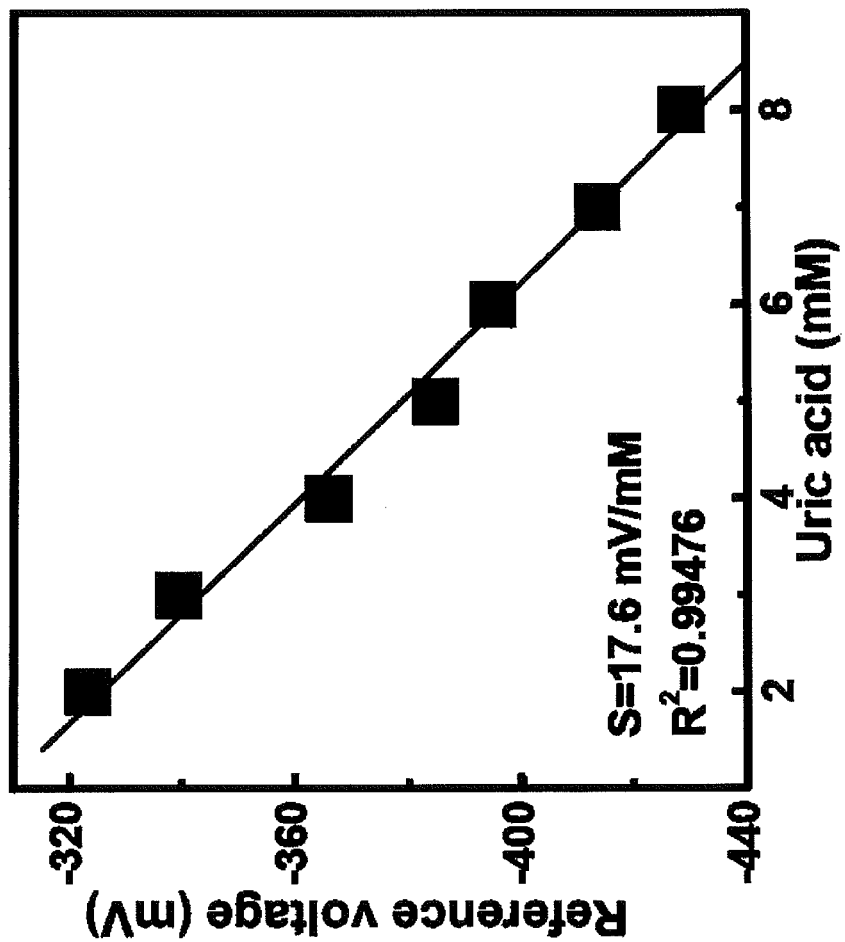
FIG. 4 plots reference voltage versus uric acid for a sensor membrane of europium titanium oxide as part of a biosensor in a preferred embodiment of the invention.
Figure 5:
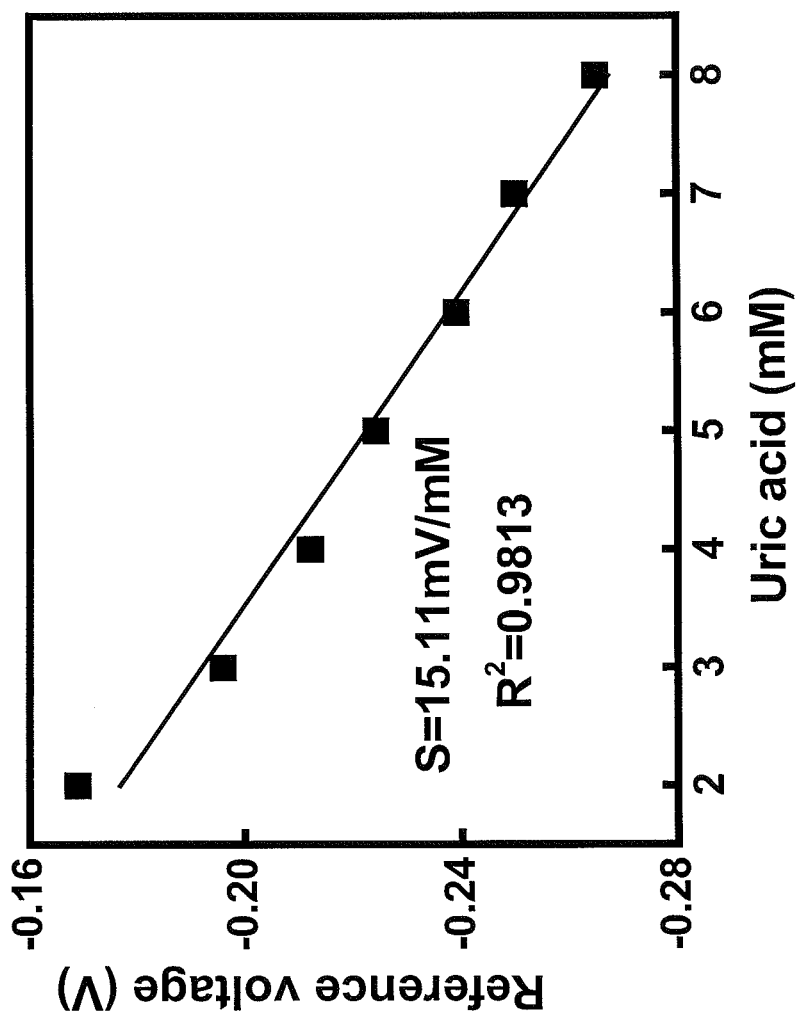
FIG. 5 plots reference voltage versus uric acid for a sensor membrane of $Tm_2Ti_2O_7$ as part of a biosensor as comparison of FIG. 4.

Referring to FIGS. 3 to 5, a biosensor 1 in accordance with the invention is shown. The biosensor 1 is an EIS sensor and comprises a sensor membrane 10 of europium titanium oxide; a semiconductor (e.g., silicon) substrate 20 with the sensor membrane 10 deposited thereon; a conductive layer 30 disposed below the semiconductor substrate 20 and including an upper electrode 301 and a lower metal conductor 302 electrically connected to both the upper electrode 301 and the sensor membrane 10; and an encapsulation member 40 surrounding the periphery and bottom of the sensor membrane 10, the semiconductor substrate 20, and the conductive layer 30, with a sensing top of the sensor membrane 10 exposed.

It is envisaged by the invention that in the detection method for the sensor membrane of europium titanium oxide as part of a biosensor by using PNIPAAm for wrapping enzymes, the enzyme is glucose, urea, lactic acid, or uric acid. The biosensor 1 is placed on a heater for heating at a constant temperature of 37° C. PNIPAAm is cured to form a white gel on the sensor membrane 10. Further, the enzyme membrane is secured onto the sensor membrane 10 prior to measurement. PNIPAAm is employed by the invention to wrap enzymes (e.g., uric acid). Furthermore, an enzyme (e.g., uric acid) membrane is formed on the wrapped enzymes due to the nature of PNIPAAm becoming a gel by heating. The uric acid membrane is used as the sensor membrane 10 of a biosensor 1 for measuring a uric acid solution.

The sensor membrane 10 of europium titanium oxide and being a part of the biosensor 1 (e.g., EIS sensor) has high sensitivity. As shown in FIG. 4, sensitivity value S=17.6 mV/mM and linearity $R^2$=0.99476. As shown in FIG. 5, as a comparison of FIG. 4, sensitivity value S=15.11 mV/mM (i.e., decrease) and linearity $R^2$=0.9813 (i.e., decrease) when $Tm_2Ti_2O_7$ is used as the sensor membrane 10 of an EIS sensor for measuring a uric acid solution.

The high dielectric nature of europium titanium oxide is taken advantage of by the invention, and a sensor membrane 10 of europium titanium oxide is a part of a biosensor (e.g., EIS sensor) 1. Further, one-use PNIAAm is employed for wrapping enzymes by a method of the invention so that not only activity of enzymes can be preserved but also sensitivity of the biosensor can be increased.

The method of the invention employing a sensor membrane 10 of europium titanium oxide as part of a biosensor (e.g., EIS sensor) 1 has the advantages of high sensitivity, high precision, and lower cost.

While the invention has been described in terms of preferred embodiments, those skilled in the art will recognize that the invention can be practiced with modifications within the spirit and scope of the appended claims.

What is claimed is:

1. A detection method comprising:
   (1) adding 1.0 g of N-isopropylacrylamide (NIPAAm) powder to 20 ml water, heating at 60° C. to form a NIPAAm solution, and cooling the NIPAAm solution to room temperature;
   (2) adding 200 µl of 98.7 wt % of ammonium peroxodisulfate (APS) and 50 µl of 99 wt % of N,N,N,N-tetramethylethylenediamine (TEMED) to the NIPAAm solution, uniformly mixing it to form a mixture, and reacting the mixture for 30 hours at room temperature to prepare a transparent gel, poly-N-isopropylacrylamide (PNIPAAm);
   (3) adding 5 mg enzymes to 100 µl of 1×PBS buffer solution, uniformly mixing it, adding 100 µl of the transparent gel, PNIPAAm to the buffer solution, and uniformly mixing the buffer solution;
   (4) placing a biosensor on a heater for heating at a constant temperature of 37° C., wherein the biosensor is an Electrolyte-insulator-Semiconductor (EIS) sensor having a sensor membrane formed of europium titanium oxide;
   (5) dropping 25 µl of the buffer solution on the sensor membrane of the biosensor for wrapping the enzymes on the sensor membrane of the biosensor;
   (6) heating and curing the wrapped biosensor to form a white gel on the sensor membrane;
   (7) placing the biosensor in a solution kept at 37° C. and keeping the white gel obtained at step (6) at 37° C.; and
   (8) taking a measurement.

2. The detection method of claim 1, wherein the biosensor is configured to detect glucose, urea, lactic acid, or uric acid.

* * * * *